US005685845A

United States Patent [19]

Grimard

[11] Patent Number: 5,685,845

[45] Date of Patent: Nov. 11, 1997

[54] STERILE RESEALABLE VIAL CONNECTOR ASSEMBLY

[75] Inventor: Jean Pierre Grimard, Vif, France

[73] Assignee: Becton, Dickinson and Company, Franklin Lakes, N.J.

[21] Appl. No.: 500,664

[22] Filed: Jul. 11, 1995

[51] Int. Cl.[6] .................... A61M 37/00; A61M 5/32

[52] U.S. Cl. .................... 604/82; 604/89; 604/416

[58] Field of Search .................... 604/82, 86, 89, 604/187, 415, 91, 416, 905, 246, 249; 141/346, 347, 348, 351; 251/325, 333, 344, 347, 349, 353; 222/129, 145, 153, 522, 525

[56] References Cited

U.S. PATENT DOCUMENTS

| | | | |
|---|---|---|---|
| 1,416,781 | 5/1922 | Bevins | 251/325 |
| 2,228,537 | 1/1941 | Smith | 128/218 |
| 2,362,165 | 11/1944 | Smith | 128/218 |
| 2,380,556 | 7/1945 | Smith | 128/218.1 |
| 4,491,876 | 1/1985 | Meyer et al. | 604/89 |
| 4,768,568 | 9/1988 | Fournier et al. | 141/286 |
| 4,865,189 | 9/1989 | Guerra et al. | 206/221 |
| 4,871,354 | 10/1989 | Conn et al. | 604/89 |
| 4,898,209 | 2/1990 | Zbed | 137/614.04 |
| 4,981,469 | 1/1991 | Whitehouse et al. | 604/86 |
| 5,088,996 | 2/1992 | Kopfer et al. | 604/415 |
| 5,125,892 | 6/1992 | Drudik | 604/90 |
| 5,158,546 | 10/1992 | Haber et al. | 604/87 |
| 5,205,821 | 4/1993 | Kruger et al. | 604/91 |
| 5,217,433 | 6/1993 | Bunin | 604/89 |
| 5,279,576 | 1/1994 | Loo et al. | 604/187 |
| 5,304,163 | 4/1994 | Bonnici et al. | 604/403 |
| 5,320,603 | 6/1994 | Vetter et al. | 604/82 |
| 5,358,501 | 10/1994 | Meyer | 604/414 |
| 5,385,545 | 1/1995 | Kriesel et al. | 604/82 |
| 5,423,791 | 6/1995 | Bartlett | 604/91 |

FOREIGN PATENT DOCUMENTS

| | | |
|---|---|---|
| 0 406 374 B11 | 8/1993 | European Pat. Off. . |
| 0 403 626 B1 | 9/1993 | European Pat. Off. . |

*Primary Examiner*—John G. Weiss
*Assistant Examiner*—David J. Cho
*Attorney, Agent, or Firm*—Vincent A. Castiglione

[57] ABSTRACT

A resealable vial connector assembly includes a transfer set having a body dimensioned for slidable insertion into a vial. The body includes an axial passageway for fluid communication into or out of the vial. A stopper support extends downwardly from the body and is dimensioned for receiving spaced apart upper and lower vial stoppers. The stopper support includes at least one passageway communicating with the axial space between the stoppers and with the passageway through the body. Upper portions of the transfer set are configured for threaded engagement with a luer collar of a medical fluid delivery instrument such as a hypodermic syringe or intravenous bag. The transfer set is configured for releasable locking engagement with the vial in a first position where both stoppers seal the entrance to the vial and in a second position where the lower stopper permits fluid communication between the vial and the passageway through the transfer set.

25 Claims, 4 Drawing Sheets

STERILE RESEALABLE VIAL CONNECTOR ASSEMBLY

BACKGROUND OF THE INVENTION

1. Field of the Invention

The subject invention relates to a sterile and resealable connector assembly for a vial that permits efficient transfer of fluid to or from the vial.

2. Description of the Prior Art

Powdered or lyophilized drugs are typically stored in sealed vials. In practice, the drug is accessed shortly prior to use by rupturing or displacing the seal. A solvent solution such as saline is then introduced into the vial to reconstitute the powdered or lyophilized drug. Once reconstituted, the drug solution is extracted from the vial for use.

Some prior an vials of powdered or lyophilized drugs include a pierceable membrane secured across the open top of the prior art vial. The membrane is normally pierced by a needle in communication with the solvent. However, care must be taken to avoid the separation of membrane fragments when the seal is pierced, as these may be accidentally delivered to the patient. These seals must typically be pierced each time access to the solvent is desired, heightening the problems associated therewith.

Other prior art vials include rubber stoppers that are urged into the vial by the needle or other device that delivers the solvent. One drawback of these stoppers is that they cannot be accessed after they have fallen into the vial, and hence the vial cannot be resealed employing the stopper originally provided. Thus, the structure of these prior an vials is not readily adapted to a vial capable of repeated opening and dosing. Where need or desire dictate that multiple access be provided to the drug held in the vial, this can be problematic. Additionally, the stopper in the vial may sometimes interfere with the subsequent flow of the drug solution.

The mixture of the solvent solution with the powdered or lyophilized drug can often generate gas. Gas pressure in the vial can cause an aerosol spray of the drug solution when the vial is being separated from the needle that delivers the solvent. An uncontrolled spraying of a drug solution is undesirable. Thus, some prior art vials include complex valves to prevent an aerosol effect. The need to prevent aerosol spraying of the drug solution further complicates the seal.

SUMMARY OF THE INVENTION

The subject invention is directed to a sterile resealable connector assembly for a vial. The connector assembly permits a user repeated access to the drug held in the vial while at the same time preserving sterility. The vial includes a closed bottom and an open top. Portions of the vial near the top define a tubular neck with an enlarged annular rim around the opening.

The connector assembly includes a transfer set with a body having opposed top and bottom ends. At least the bottom end of the body is dimensioned for slidable insertion into the open top of the vial. To provide fluid access to and from the interior of the vial, a fluid access device such as a luer connector hub projects axially from the top end of the body and a stopper support projects from the bottom end. A fluid passageway extends through the transfer set from the luer connector hub to an opening such as a lateral opening located intermediate the length of the stopper support.

A flange may be provided which projects outwardly from the top end of the body of the transfer set. One or more legs may be disposed to project downwardly from the flange. The legs are oriented to surround the annular rim of the vial when the body of the transfer set is in the open top of the vial. Portions of the legs remote from the flange may include grippers to lockingly engage the rim of the vial and to resist separation of the transfer set from the vial.

The legs may further include means for holding the transfer set in either an upper position, where the vial is sealed, or a lower position, where fluid communication to the vial is possible. In one embodiment, the holding means may comprise resiliently deflectable clips. The clips may hold the annular rim between the clips and the grippers when the transfer set is in the upper position. The clips may then be resiliently deflected to move the transfer set into the lower position where fluid communication into the vial can be achieved. Alternatively, in another embodiment, the holding means may include an array of internal threads which are threadedly engageable with outwardly disposed regions on the rim of the vial for moving the transfer set between the upper and lower positions.

The connector assembly may further include at least one external seal for sealing the open top end of the vial prior to initial use of the connector. The external seal may be a cap removably engaged around the transfer set and/or removably engaged with portions of the vial. The cap further prevents accidental activation of the transfer set until use is desired. If desired, the engagement of the cap to the vial may include a tamper evident closure. Alternatively or additionally, a luer lock seal may be provided which is threadedly engageable with the luer connector hub of the transfer set.

The connector assembly of the subject invention further includes upper and lower stoppers, preferably mounted in axially spaced relationship to the stopper support of the transfer set. The stoppers, which can be formed in a generally annular configuration, are dimensioned for sliding sealing engagement with the opening to the vial. The axial dimensions of the lower stopper and the axial length of the stopper support are selected to permit the lower stopper to be moved sufficiently into the vial for permitting fluid flow between the upper and lower stoppers and into the vial when the transfer set is moved into its lower position.

The transfer set of the connector is initially maintained in its upper position such that both stoppers are sealingly engaged in the open top to the vial. Redundant initial sealing is further achieved by the external seal. Powdered or lyophilized drugs stored in the vial may be accessed by removing the cap and luer lock seal if provided, and moving the transfer set into its lower position on the vial. Movement of the transfer set into the lower position causes the lower stopper to move out of sealing engagement with the neck of the vial, and places the passageway through the transfer set in fluid communication with the interior of the vial. A solvent may thereafter be introduced via the passageway to reconstitute the powdered or lyophilized drugs stored in the vial.

The vial can be resealed by merely urging the transfer set back to the upper position so that the lower stopper sealingly engages the neck of the vial. This upward movement of the transfer set can be achieved by disengaging the clips on the legs of the transfer set or by threadedly moving the transfer set relative to the vial. The drug solution that has been resealed can be accessed as needed by merely urging the transfer set downwardly again as described above.

DETAILED DESCRIPTION OF THE PREFERRED EMBODIMENTS

Figure 1:
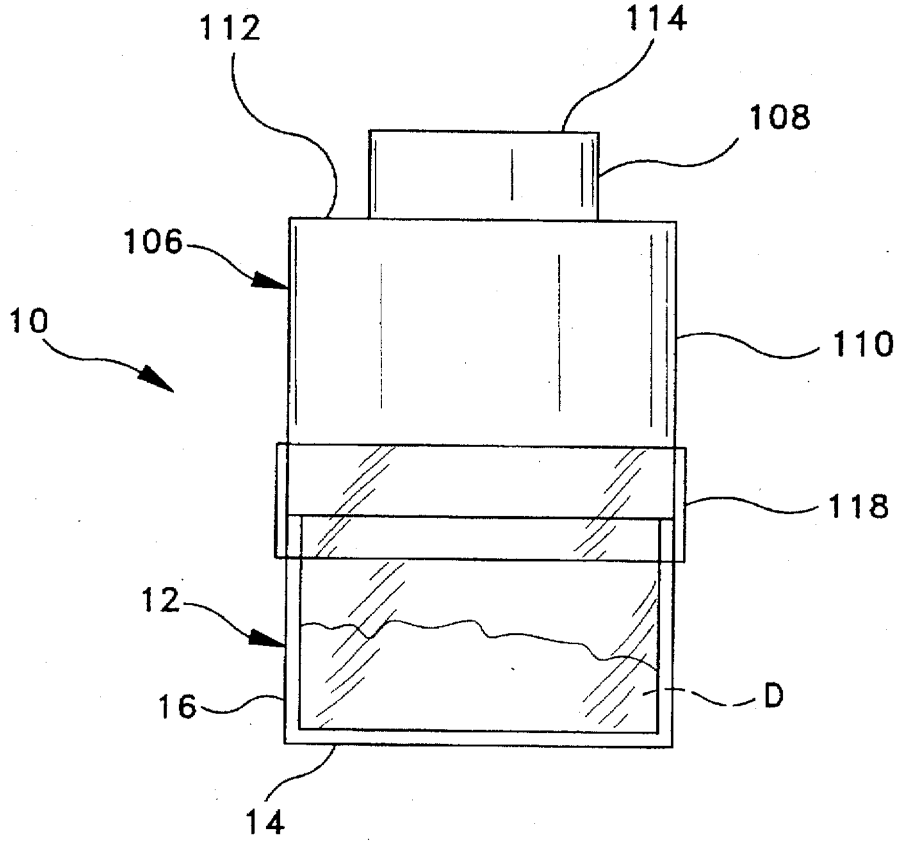
FIG. 1 is a side elevational view of a vial and a vial connector assembly in accordance with the subject invention.
Figure 2:
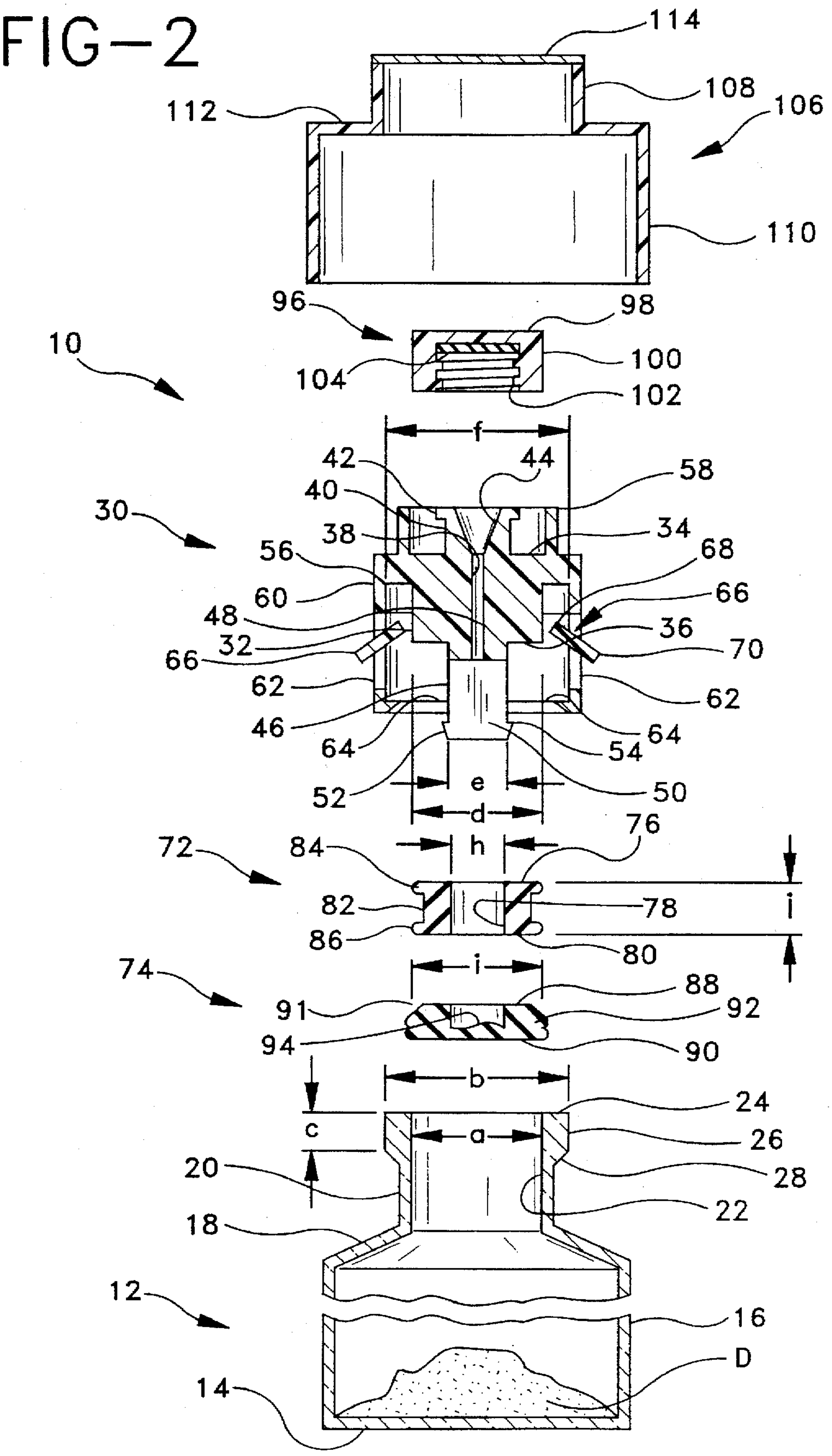
FIG. 2 is an exploded longitudinal cross-sectional view of the vial and connector assembly in FIG. 1.

A connector assembly in accordance with the subject invention is identified generally by the numeral 10 in FIGS. 1–4. Connector assembly 10 is used with a vial 12 which may be unitarily formed from glass, medical grade plastics, or like materials. Vial 12 includes a circular bottom wall 14 and a cylindrical side wall 16 extending upwardly therefrom. An annular shoulder 18 extends inwardly from portions of side wall 16 remote from bottom wall 14. A tubular neck 20 extends upwardly from inner portions of shoulder 18, and defines an inner cylindrical surface 22 of diameter "a". Neck 20 terminates at a top 24 which is open and provides communication to interior portions of vial 12. Portions of neck 20 adjacent top 24 are characterized by an enlarged annular rim 26 having a generally radially aligned locking surface 28 facing shoulder 18. Rim 26 defines an outside diameter "b" and an axial length "c" as shown in FIG. 2.

Figure 3:
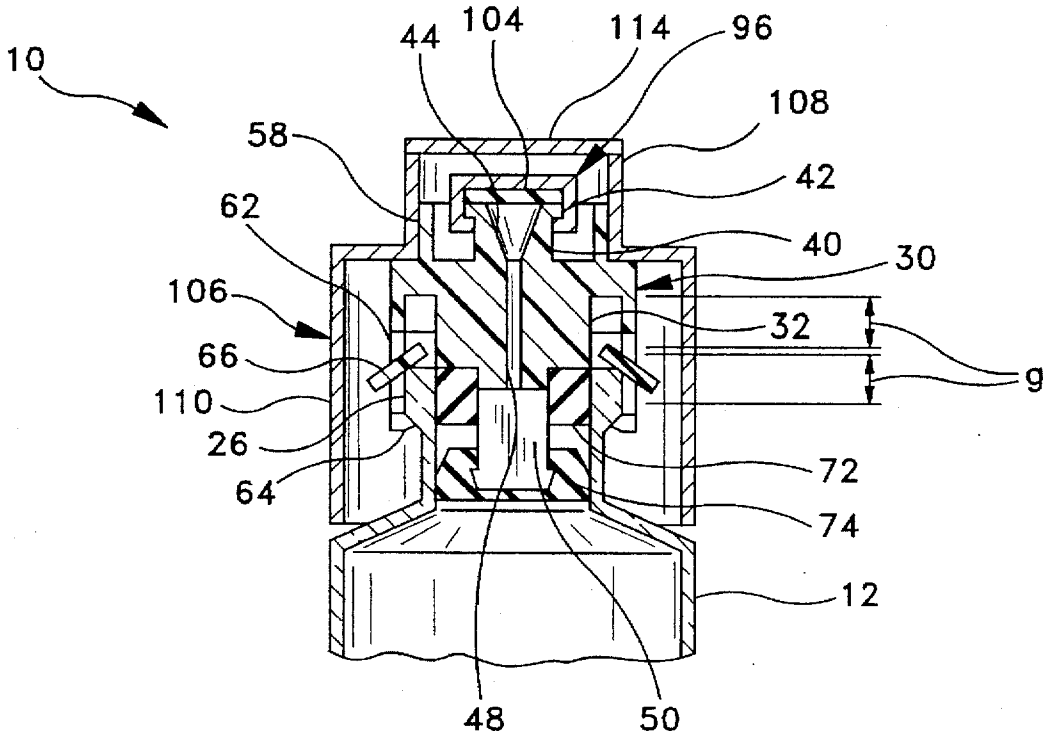
FIG. 3 is a cross-sectional view of the connector assembly of FIG. 2 in the upper position on the vial.
Figure 4:
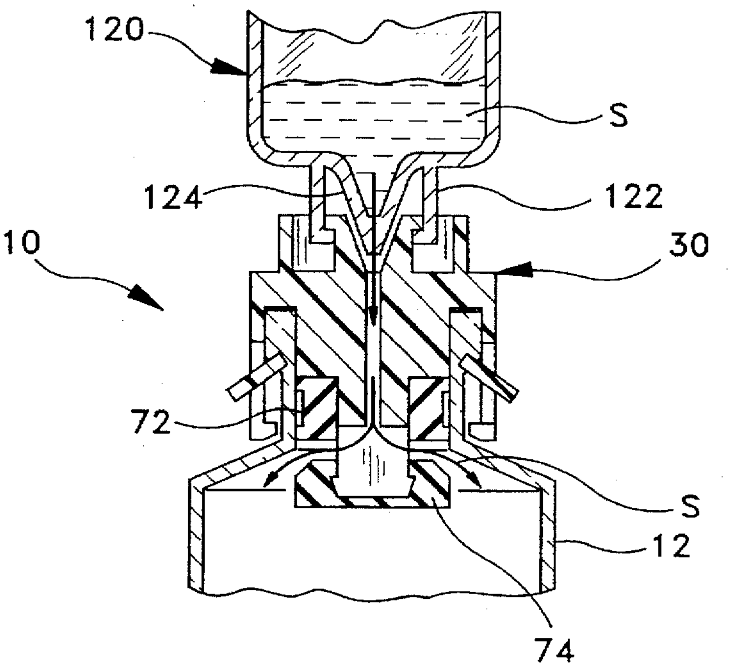
FIG. 4 is a cross-sectional view similar to FIG. 2 but showing the connector assembly in the lower position.

Connector assembly 10 includes a transfer set 30 as shown in FIGS. 2–4. Transfer set 30 may be unitarily molded from a thermoplastic material such as a medical grade plastic and includes a generally cylindrical body 32 with a diameter "d" slightly less than inside diameter "a" defined of neck 20 on vial 12. Thus, body 32 of transfer set 30 can be slidably advanced into open top end 24 of vial 12. Body 32 of transfer set 30 includes opposed top and bottom ends 34 and 36, respectively, and a fluid passage 38 extending axially therebetween.

To provide a fluid conduit to and from the interior portions of vial 12, a fluid access device such as a luer connector hub 40 may be provided. Here, luer connector hub 40 projects axially upwardly from top end 34 of body 32. Luer connector hub 40 includes an outward projection 42 spaced from top end 34 of body 32 for threaded engagement with a luer lock collar or a comparably configured threaded sealing stopper. Luer connector hub 40 further includes a flared entry 44 extending therethrough and communicating with fluid passage 38 of body 32. While the fluid access device is herein depicted as a luer connector hub, it will be appreciated and understood by those skilled in the art, that the fluid access device need not be limited to a luer connector hub. For instance, the fluid access device can entail a needle arrangement as shown, for instance, in U.S. Pat. No. 5,358,501 to Meyer. Alternately, a spike-type arrangement may be provided, for instance, to provide fluid communication to and from vial 12 where the source of solvent is provided with a pre-slit-type membrane. Other configurations are readily envisionable.

A stopper support 46 projects axially downwardly from bottom end 36 of body 32. Stopper support 46 may be formed in a generally cylindrical configuration along most of its length. Stopper support 46, defining a diameter "e", includes an axially aligned fluid passage 48 that communicates with the fluid passage 38 of body 32. Portions of stopper support 46 spaced away from body 32 include fluid openings 50 which, as shown, may be laterally formed respective of the stopper support. Fluid openings 50 communicate with axial fluid passages 38 and 48, and permit fluid flow into or out of regions of transfer set 30 surrounding stopper support 46. Portions of stopper support 46 remote from body 32 define an enlarged frustoconical head 52 having a sharp annular edge 54 facing body 32.

Transfer set 30 further includes an annular flange 56 projecting transversely from top end 34 of body 32. A cylindrical wall 58 projects upwardly from flange 56 in surrounding relationship to luer connector hub 40. A cylindrical skirt 60 projects downwardly from flange 56 and in surrounding relationship to body 32. Skirt 60 defines an inside diameter "f" which is slightly greater than outside diameter "b" of rim 26 on vial 12. Thus, skirt 60 can be telescoped around rim 26 as body 32 is slid into neck 20 of vial 12.

One or more gripper legs 62 may be formed to extend downwardly from skirt 60. At least one of gripper legs 62 is provided with an inwardly projecting gripper 64 at the terminus of the leg. As depicted herein, where there are one or more gripper legs 62, they may be configured so as to be spaced from one another. However, in other variations, gripper legs 62 may define continuous extensions of skirt 60 that are separated from one another by narrow slots to permit the outward deflection relative to skirt 60.

Legs 62 may be characterized by resiliently deflectable clips 66 and, as herein shown, at least one of the legs, preferably that leg provided with gripper 64, is provided with a clip 66. Clips 66 can be formed or otherwise molded separate from legs 62, or if desired, as an integral part of legs 62. Clip 66 includes a lock 68 and an actuator 70. Lock 68 of clip 66 is spaced from flange 56 by a distance "g" which is approximately equal to axial length "c" of rim 26 on vial 12. Lock 68 of clip 66 is further spaced from gripper 64 on the corresponding leg 62 by substantially the same distance "g". In the unbiased condition shown in FIG. 3, locks 68 extend inwardly from legs 62. However, actuators 70 can be urged radially inwardly to cause clips 66 to pivot relative to legs 62. Where the clip 66 is formed as part of legs 62, this can be effected, for instance, by the formation of a "living hinge" during the molding process. Inward pivoting of actuators 70 of clips 66 causes a corresponding outward pivoting of locks 68. However, a release of the forces required to generate this pivoting movement will cause clips 66 to resiliently return toward an undeflected condition as shown in FIG. 4.

Connector assembly 10 further includes upper and lower stoppers 72 and 74, each of which may be unitarily molded from a suitable thermosetting elastomer, such as natural rubber, or various thermoplastic elastomers. Upper stopper 72 is generally annular, and includes opposed axial ends 76 and 78, an inner cylindrical surface 80 and an opposed outer surface 82. Inner cylindrical surface 80 defines a diameter "h" which, in an unbiased condition, is equal to or slightly less than diameter "e" of stopper support 46. Thus, upper stopper 72 can be urged onto stopper support 46 with inner surface 80 of upper stopper 72 being in fluid tight engagement with stopper support 46. Outer surface 82 of upper stopper 72 is characterized by at least one annular rib which engages with neck 20 of the vial. Here, two annular fibs 84 and 86 are provided which define outer diameters "i" that are equal to or slightly greater than inside diameter "a" of neck 20 on vial 12. Thus, upper stopper 72 can be slid into fluid tight engagement with neck 20 of vial 12. Ribs 84 and 86 on upper stopper 72 are spaced from one another by a distance "j" which is greater than the length of travel of transfer set 30 between its upper and lower positions.

Lower stopper 74 may be formed as a cylinder with opposed axial ends 88 and 90 defining between them an axial thickness "m" and an outer circumferential surface 92 having an outside diameter "i". As herein depicted, lower stopper 74, however, does not include an aperture extending entirely therethrough as in upper stopper 72. Rather, lower stopper 74 includes a mounting aperture 94 extending into end 88 and terminating short of end 90. Aperture 94 is dimensioned to receive frustoconical head 52 on stopper support 46. Aperture 94 is further defined by a pair of protrusions 95 adjacent end 88 of the lower stopper. As herein configured, the material forming lower stopper 74 yields to allow aperture 94 to accept sharp annular edge 54. After edge 54 has passed into aperture 94, the material of stopper 74 will resiliently return toward an unbiased condition, allowing protrusions 95 to grippingly engage around edge 54. Outer circumferential regions adjacent end 88 and outer circumferential surface 92 are chamfered at location 91 to provide a path for fluid flow, as well as to assist in backward movement of the lower stopper during resealing. It will, of course, be appreciated by the skilled artisan that in lieu of the annular edge 54/aperture 94 connection herein described between the stopper support and the lower stopper, a conventional threaded arrangement may also be employed.

Connector assembly 10 further may also feature a luer lock seal 96 to preserve sterility of the luer lock hub 40 pending use. In one configuration, luer lock seal 96 features a circular end wall 98 and a cylindrical side wall 100 with internal threads 102 configured for threadedly engaging luer lock hub 40 on transfer set 30. A suitable sealing material 104 such as a rubber seal is secured to the interior face of wall 98. Thus, luer lock seal 96 can be threadedly engaged onto luer lock hub 40 and tightened such that sealing material 104 sealingly engages the end of luer lock hub 40 to define a barrier over passage 44, which if uncovered, would otherwise provide communication between upper and lower stoppers 72 and 74 and thereafter, to the interior of vial 12 when the device is activated. Other configurations of the luer lock seal are envisionable.

Connector assembly 10 may also include a cap 106 with a small diameter cylindrical top end 108 dimensioned to seal around cylindrical wall 58 of transfer set 30. Cap 106 further includes a large diameter cylindrical end 110 connected to small diameter end 108 by a step wall 112. Large diameter end 110 is dimensioned to engage cylindrical side wall 16 of vial 12. While cap 106 can be formed in an integral manner with a solid top 114, as herein depicted, top 114 may be formed as a removable or peelable seal **114*a* extending across small diameter end 108**.

Vial connector assembly 10 may be assembled by mounting, under conditions of sterility, lower stopper 74 into vial neck 20. Thereafter, still under conditions of sterility, upper stopper 72 may be mounted onto stopper support 46 of transfer set 30 such that end 76 of upper stopper 72 is adjacent bottom end 36 of body 32. Luer lock seal 96 may then be threadedly engaged onto luer lock hub 40 and tightened sufficiently for seal 104 to engage against luer lock hub 40.

Still under conditions of sterility, stopper support 46 is inserted into vial neck 20 such that annular edge 54 is engaged by the material of lower stopper 74 adjacent aperture 94. In this condition, an annular space 116 having an axial length "x" exists between upper and lower stoppers 72 and 74 as shown in FIGS. 3 and 4. Annular space 116 aligns with the one or more openings 50 in stopper support 46 to permit fluid communication between the interior of vial 12 and axial aligned passageways 48 and 38 of transfer set 30.

As assembly 10 is mounted to vial 12, legs 62 are simultaneously telescoped over annular rim 26 of vial 12. Grippers 64 will cause legs 62 to deflect outwardly and over annular rim 26 on vial 12. Thus, annular rim 26 of vial 12 will be engaged between grippers 64 and locks 68 of clips 66. Vial 12 is efficiently sealed in this condition. More particularly, stoppers 72 and 74 substantially prevent gas communication adjacent inner cylindrical surface 22 of neck 20 on vial 12. Additionally, lower stopper 74 prevents gas communication from interior regions of vial 12 to the interconnected axial passageways 38 and 48 extending through transfer set 30. Still further, luer lock seal 96 provides redundant sealing of passageways through transfer set 30. Thus, the passages through transfer set 30 are effectively closed.

Additional sealing of vial 12 can further be provided by sliding small cylindrical end 108 of cap 106 over cylindrical wall 58 on transfer set 30. This close engagement, combined with seal **114*a* across small cylindrical end 108 of cap 106, contributes to further sealing. Still further, cap 106 may prevent any inadvertent contact with transfer set 60 that could move transfer set 30 from the upper position described above. A tamper evident tape 118 may be provided across the interface of cap 106 and vial 12 to provide evidence of opening as shown in FIG. 1**.

Connector assembly 10 is used by initially removing or rupturing tamper evident tape 118. Cap 106 is then removed from transfer set 60. Luer lock seal 96 may then also be removed. Drug D in vial 12 may be mixed with a solvent S delivered by a source 120 such as hypodermic syringe or an intravenous fluid bag, provided with means for mating to luer lock hub 40, or the like. As herein depicted, source 120 is configured as a hypodermic syringe having a luer lock attachment 122 which may be threadedly engaged with luer lock hub 40 such that tip 124 of hypodermic syringe 120 communicates with tapered entry 44 of luer lock hub 40 and with axial passageways 38 and 48 in transfer set 30. However, communication between solvent S in syringe 118 and drug D in vial 12 is prevented by lower stopper 74.

Solvent S can be delivered to drug D by moving transfer set 30 downwardly into neck 20. This downward movement causes locks 68 of clips 66 to deflect outwardly, permitting skirt 60 to pass over annular rim 26 of vial 12, such that locks 68 of clips 66 will re-lock with locking surface 28 of rim 26. Simultaneously, lower stopper 74 moves beyond neck 20 towards the interior regions of the vial. Chamfered corner 91 on lower stopper 74 contributes to free fluid communication between the interior of vial 12 and portions of openings 50 between upper and lower stoppers 72 and 74. As herein shown, the length of movement of transfer set 30 is equal to the distance "g" from lock 68 to flange 56, plus the axial motion of lock 68 as it engages locking surface 28 of annular rim 26. This length of movement is selected to exceed the axial thickness "m" of lower stopper 74 but to be less than the axial length "j" on upper stopper 72. Thus, as shown in FIG. 4, vial 12 can be accessed, while upper stopper 72 remains engaged in neck 20 of vial 12, maintaining sterility.

The plunger (not shown) of hypodermic syringe 120 can be urged downwardly for forcing solvent S in hypodermic syringe 120 through axial passageways 38 and 48, through opening 50 and into vial 12 for mixing with drug D. The diluted drug D can thereafter be aspirated into hypodermic syringe 120 for use.

In other instances, it may be desirable to disconnect hypodermic syringe 120 from vial 12 and to make another connection with apparatus for delivering the drug solution to a patient. In still other instances, only a portion of the drug solution may be used at one time, and remaining portions may be retained for subsequent use. In these situations, a drug solution may be resealed by exerting inward pressure on actuator portion 70 of clip 66 for disengaging locking portion 68 thereof from locking surface 28 on rim 26 of vial 12. Transfer set 30 may then be urged upwardly relative to vial 12 such that annular rim 26 is lockingly engaged between grippers 64 and locks 68 of clip 66. In this condition, lower stopper 74 will sealingly engage again with inner cylindrical surface 22 of neck 20 on vial 12. Chamfered corner 91 contributes to smooth, resealing motion of lower stopper 74 with vial neck 20. Hypodermic syringe 120 then can be threadedly disengaged from luer lock hub 40. The sealing engagement of lower stopper 74 with neck 20 of vial 12 will prevent or minimize any aerosol dispersion of drug solution that might otherwise be caused by gas generated during the mixture of solvents and drug D.

As the skilled artisan will appreciate, depending upon the conditions of use for the assembly, there may be occasion when a region 150 of vial neck 20, located above upper stopper 72 when the upper stopper is in its lower position respective of vial neck 20, may become subject to contaminants detrimental to sterility of the drug D. See FIGS. 4 and 5. It is thus a feature of the connector assembly 10 to prevent contaminants in region 150 from being pulled into the fluid path and into contact with drug D during subsequent resealing of the assembly. It will be realized that if the axial length "x" of annular space 116 is selected to be greater than the length of movement of transfer set 30, upper stopper 72 can remain in its lower position in vial neck 20 so as to avoid contact with region 150. The various components can be designed or otherwise selected so that the frictional force exerted between inner cylindrical surface 80 and stopper support 46 is less than the frictional force between the outer surface 82 and vial neck 20. Thus, as transfer set 30 is urged upwards, upper stopper 72 can remain fixed in its lower position relative to vial neck 20, while allowing stopper support 46 and lower stopper 74 to retract to their original upper position. Upper and lower stoppers 72, 74 will be disposed adjacent one another, largely eliminating annular space 116 during reseating (See FIG. 5), and neither of the stoppers disturbs region 150 of the vial neck. In this manner, upper stopper 72 is prevented from inadvertently tracking any contaminants from region 150 of the vial neck. When the transfer set 30 is reactivated, lower stopper 74/stopper support 46 will advance relative to the now fixed upper stopper 72, without contact with region 150, so as to re-establish annular space 116 and, hence, re-open the fluid path. By this configuration, it will be realized that only one annular rib need be provided on upper stopper 72 for engagement with vial neck 20.

Figure 5:
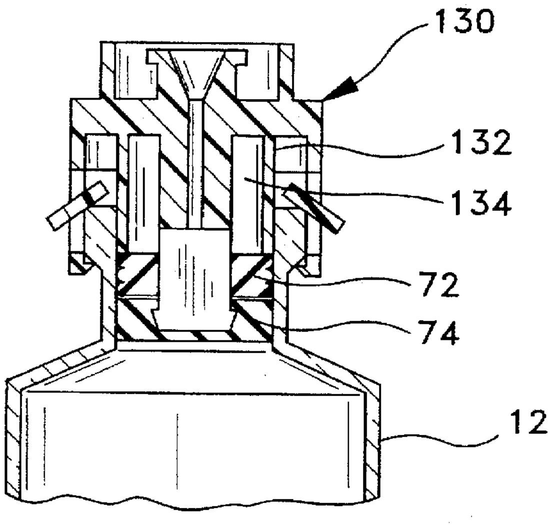
FIG. 5 is a cross-sectional view similar to FIG. 4 but showing an alternate connector assembly.

FIG. 5 shows an alternate embodiment 130 of a transfer set for use as described above and shown, for instance, where the embodiment 130 has been reseated with upper stopper 72 maintained in its lower position. It will be noted that the only significant difference between transfer set 130 and the above described transfer set 30 relates to the body. In particular, transfer set 130 includes a body 132 that is partly hollowed to define a chamber 134. Chamber 134 can alleviate overpressurized conditions within vial 12 and/or set 30 by accommodating aerosol or gaseous dispersion that might result from a solvent S and drug D mixture in the space 116 between the upper and lower stopper 72 and 74. Thus, aerosol dispersion to external regions after separation of the hypodermic syringe or other connection from transfer set 130 is less likely.

Figure 6:
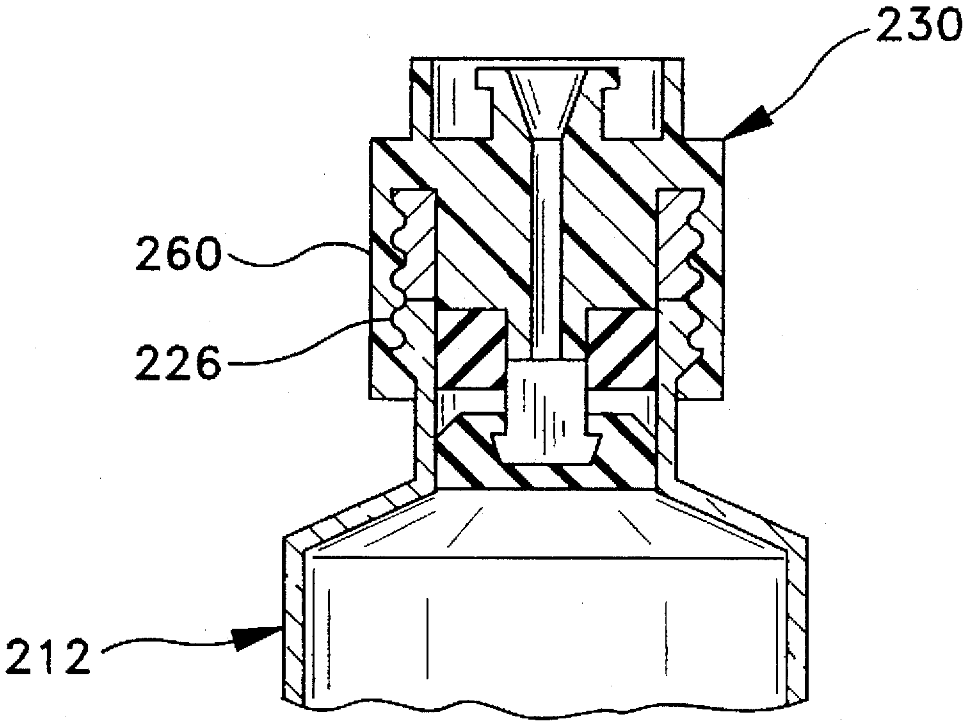
FIG. 6 is a cross-sectional view similar to FIG. 4 but showing a second alternate connector assembly and vial.

FIG. 6 shows another alternate transfer set 230 which differs from the above described transfer set 30 in that it includes an internal threaded skirt 260 in place of the legs 60 and clips 66 shown above. Transfer set 260 is used with a vial 212 having an annular rim 226 with external threads. The skirt 260 can be threadedly moved on rim 226 between the upper and lower positions as described above.

It will be appreciated and understood by those skilled in the art that further and additional forms of the invention may be devised without departing from the spirit and scope of the appended claims, the invention not being limited to the specific embodiments shown.

What is claimed is:

1. A connector assembly for a vial having an interior, a neck defining an open top to said vial and an annular rim around portions of said neck surrounding said open top, said connector assembly comprising:

a transfer set comprising a body with opposed top and bottom ends, at least said bottom end being dimensioned for slidable movement between upper and lower positions in said neck of said vial, a fluid access device extending from said top end of said body and a stopper support extending from said bottom end, a passageway extending through said transfer set from said fluid access device to an opening located on said stopper support, one or more legs supported in spaced relationship to said body, at least one of said legs including a manually deflectable clip for selective locking engagement with said annular rim of said vial in either of said upper and lower positions; and upper and lower stoppers mounted in spaced relationship on said stopper support such that said opening of said passageway is intermediate said stoppers, said upper stopper being dimensioned and disposed for sealing engagement with said neck of said vial in both said upper and lower positions of said transfer set, said lower stopper being dimensioned and disposed on said stopper support for spaced relationship with said neck of said vial when said transfer set is in said lower position so that said opening of said passageway communicates with said interior of said vial and for sealing engagement with said neck of said vial when said transfer set is in said upper position to seal said opening from said interior of said vial.

2. The connector assembly of claim 1, wherein said fluid access device comprises a luer connector hub.

3. The connector assembly of claim 2, further comprising at least one external seal releasably engaged with said transfer set for sealing portions of said passageway adjacent said luer connector hub.

4. The connector assembly of claim 3, wherein said external seal comprises a luer lock seal having a top wall and an annular side wall projecting from said top wall, said annular side wall including an array of internal threads selectively engageable with said luer connector hub of said transfer set, and a seal secured to portions of said bottom wall surrounded by said annular wall of said luer lock seal for sealingly engaging portions of said luer connector hub.

5. The connector assembly of claim 1, further comprising a cap releasably engaged around said transfer set and covering said fluid access device.

6. The connector assembly of claim 5, wherein said cap engages said vial.

7. The connector assembly of claim 3, wherein said external seal comprises a cap sealing portions of said passageway in said luer connector hub and surrounding said transfer set.

8. The connector assembly of claim 7, wherein said cap engages said vial.

9. The connector assembly of claim 1, wherein said lower stopper includes an annular side wall dimensioned for sealing engagement with said neck of said vial and a top wall in spaced relationship to said upper stopper, and a chamfered edge being defined between said top wall and said annular side wall.

10. The connector assembly of claim 1, wherein said manually deflectable clip includes an actuator disposed externally on said transfer set for selectively releasing said clip from said annular rim.

11. The connector assembly of claim 1, wherein said upper and lower positions of said transfer set are defined by a selected distance of movement, said upper stopper including an outer circumferential surface having at least one annular rib therewith for engagement with the neck of the vial in each of the upper and lower positions.

12. The connector assembly of claim 1, wherein said upper and lower positions of said transfer set are defined by a selected distance of movement, said upper stopper including an outer circumferential surface having at least one annular rib formed thereon.

13. The connector assembly of claim 1, wherein said upper and lower positions of said transfer set are defined by a selected distance of movement, said upper stopper including an outer circumferential surface having at least one pair of annular ribs formed thereon, said annular ribs being spaced from one another by a distance greater than said selected distance of movement of said transfer set between said upper and lower positions on said vial.

14. The connector assembly of claim 1, wherein said transfer set includes a flange projecting outwardly from said top end of said body, said one or more legs projecting from said flange in spaced relationship to said body, wherein at least one of said legs includes a gripper spaced from said flange and being dimensioned for gripping said annular rim of said vial when said transfer set is in said upper position.

15. The connector assembly of claim 14, wherein said manually deflectable clip is disposed intermediate said gripper of said at least one leg and said flange, said clip configured for releasably locking said annular rim of said vial between said gripper and said clip when said transfer set is in said upper position, and being configured for releasably locking said annular rim of said vial between said clip and said flange when said transfer set is in said lower position.

16. The connector assembly of claim 1, wherein said transfer set is unitarily formed from a thermoplastic material.

17. The connector assembly of claim 1, wherein said body of said transfer set includes a generally annular hollow chamber extending upwardly into said bottom end for accommodating aerosol or gaseous dispersion from said vial.

18. A connector assembly for a vial having an interior, a neck defining an open top to said vial and an externally threaded annular rim around portions of said neck surrounding said open top, said connector assembly comprising:

a transfer set having a body with opposed top and bottom ends, at least said bottom end being dimensioned for slidable movement between upper and lower positions in said open top of said vial, a fluid access device extending from said top end of said body and a stopper support extending from said bottom end, a passageway extending through said transfer set from said fluid access device to an opening located on said stopper support, a generally cylindrical skirt supported in spaced relationship around said body, said skirt including an array of internal threads threadedly engageable with said threads on said annular rim of said vial, said threads extending axially a sufficient distance for moving said body between said upper and lower positions in said open top of said vial; and upper and lower stoppers mounted in spaced relationship on said stopper support such that said opening of said passageway is intermediate said stoppers, said upper stopper being dimensioned and disposed for sealing engagement with said neck of said vial in both said upper and lower positions of said transfer set, said lower stopper being dimensioned and disposed on said stopper support for spaced relationship from the neck of said vial when said transfer set is in said lower position so that said opening of said passageway communicates with said interior of said vial and for sealing engagement with said neck of said vial when said transfer set is in said upper position to seal said opening from said interior of said vial.

19. The connector assembly of claim 18, further comprising at least one external seal releasably engaged with said transfer set for sealing portions of said passageway adjacent said fluid access device.

20. The connector assembly of claim 19, wherein said body of said transfer set includes a generally annular hollow chamber extending upwardly into said bottom end for accommodating aerosol or gaseous dispersion from the vial.

21. A connector assembly for a vial having an interior, a neck defining an open top to said vial and an annular rim around portions of said neck surrounding said open top, said connector assembly comprising:

a transfer set having a body with opposed top and bottom ends, at least said bottom end being dimensioned for slidable movement a selected distance between upper and lower positions in said neck of said vial, said stopper support extending from said bottom end of said body, an axial passageway extending through said transfer set from said top end to an opening located on said stopper support; and upper and lower stoppers mounted in spaced relationship on said stopper support such that said opening of said passageway is intermediate said stoppers, said upper stopper having a length greater than said selected distance of movement of said transfer set between said upper and lower positions and being disposed for sealing engagement with said neck of said vial in both said upper and lower positions of said transfer set, said lower stopper being dimensioned and disposed on said stopper support for sealing engagement with said neck of said vial when said transfer set is in said upper position to seal said opening from said interior of said vial and being spaced below said neck when said transfer set is in said lower position so that said opening communicates with said interior of said vial.

22. The connector assembly of claim 21, wherein said upper stopper includes an outer circumferential surface having a pair of axially spaced ribs dimensioned for sealing engagement with said neck of said vial, said ribs being spaced by a distance greater than said selected distance of movement of said transfer set between said upper and lower positions.

23. The connector assembly of claim 21, wherein said lower stopper includes an outer circumferential surface sealingly engaged with said neck of said vial when said transfer set is in said upper position and having a top wall facing said upper stopper, a chamfered edge being defined intermediate said circumferential wall of said lower stopper and said top wall thereof.

24. The connector assembly of claim 21, wherein said transfer set includes engaging means for engaging said annular rim of said vial in each of said upper and lower positions of said transfer set.

25. The connector assembly of claim 24, wherein said engaging means comprises an annular flange projecting outwardly from said top end of said body, one or more legs projecting downwardly from said annular flange in spaced relationship to said body, wherein each of said one or more legs comprise ends remote from said flange including grippers dimensioned for engaging said annular rim when said transfer set is in said upper position and manually deflectable clips disposed on said legs intermediate said grippers and said annular flange, said manually deflectable clips being disposed and dimensioned to releasably lock said annular rim between said clips and said grippers when said transfer set is in said upper position and to releasably lock said annular rim between said clips and said flange when said transfer set is in said lower position.

* * * * *